US006008260A

United States Patent [19]
Pezzuto et al.

[11] Patent Number: 6,008,260
[45] Date of Patent: Dec. 28, 1999

[54] CANCER CHEMOPREVENTATIVE COMPOSITION AND METHOD

[75] Inventors: John M. Pezzuto, River Forest, Ill.; Richard C. Moon, Plant City, Fla.; Mei-Shiang Jang, Chicago, Ill.

[73] Assignee: Pharmascience, Quebec, Canada

[21] Appl. No.: 09/005,114

[22] Filed: Jan. 9, 1998

[51] Int. Cl.$^6$ .................................................. A61K 31/05
[52] U.S. Cl. .......................................... 514/733; 514/736
[58] Field of Search ...................................... 514/733, 736

[56] References Cited

U.S. PATENT DOCUMENTS

| | | | |
|---|---|---|---|
| 5,411,986 | 5/1995 | Cho et al. | 514/514 |
| 5,747,536 | 5/1998 | Cavazza | 514/733 |

OTHER PUBLICATIONS

Sanders et al., Book of Bbstracts, 214th ACS National Meeting, Am. Chem. S., Sep. 7, 1997.

Miura et al., Igaku no Ayumi, 183(8), 530–536 Abstract Only, 1997.

Jang et al., Science, 275(5297), 218–220 Abstract Only, 1997.

J.R. Landolph, "Chemical transformation in C3H 10T½ C18 mouse embryo fibroblasts: historical background, assessment of the transformation assay, and evolution and optimization of the transformation assay protocol," pp. 185–199, in "Transformation Assay of Established Cell Lines," T. Kakunaga et al., eds., Oxford Univ. Press, Toronto (1985).

R.J. Kulmacz et al., "Cyclo–oxygenase: measurement, purification and properties," pp. 209–277, in "Prostaglandins and Related Substances" (IRL Press, Oxford), (1987).

C.A. Reznikoff et al., "Quantitative and qualitative studies of chemical transformation of cloned C3H mouse embryo cells sensitive to postconfluence inhibition of cell division," *Cancer Res.*, 33, 3239–3249, Dec. 1973.

O.J. Plescia et al., "Subversion of immune system by tumor cells and role of prostaglandins," *Proc. Nat. Acad. Sci., USA,* vol. 72, No. 5, pp. 1848–1851, May, 1975.

S. Mondal et al., "Two–stage chemical oncogenesis in cultures of C3H/10T1/2 cells," *Cancer Res.,* 36, 2254–2260, Jul. 1976.

J.S. Bertram, "Reduction in the formation of carcinogen–induced transformed foci by penicillin G sodium in the C3H/10T$_{1/2}$ CL8 cell line," *Cancer Lett.,* 7, 289–298 1979.

M.B. Sporn et al., "Chemoprevention of cancer with retinoids," *Federation Proceedings,* vol. 38, No. 11, 2528–2534, Oct. 1979.

F.J.G. van der Ouderaa et al., "Purification of PGH synthase from sheep vesicular glands," *Methods Enzymol.,* 86, 60–68, 1982.

T.V. Zenser et al., "Prostaglandin H synthase–catalyzed activation of benzidine: a model to assess pharmacologic intervention of the initiation of chemical carcinogenesis," *J. Pharmcol. Exp. Ther.,* vol. 227, No. 3, 545–550, 1983.

J.S. Goodwin, "Immunologic effects of nonsteroidal antiinflammatory drugs," *Am. J. Med.,* 77, 7–15, 1984.

D. Wild et al., "Prostaglandin H synthase–dependent mutagenic activation of heterocyclic aromatic amines of the IQ–type," *Carcinogenesis,* vol. 8, No. 4 541–545, 1987.

H.J. Prochaska et al., "Direct measurement of NAD-(P)H:quinone reductase from cells cultured in microtiter wells: a screening assay for aniticarcinogenic enzyme inducers," *Anal. Biochem.,* 169, 328–336, 1998.

R.C. Moon et al., "Retinoid inhibition of experimental carcinogenesis," *Chemistry and Biology of Retinoids,* M.I. Dawson et al., eds., CRC Press, Boca Raton, FL, 501–518, 1990.

E. Mannilla et al., "Anti–leukaemic compounds derived from stilbenes in *Picea abies* bark," *Phytochemistry,* 33, 813–816, 1993.

G.S. Jayatilake et al., "Kinase inhibitors from polygonum cuspidatum," *J. Nat. Prod.,* vol. 56, No. 10. 1805–1810, Oct. 1993.

L.W. Wattenberg, "Prevention–therapy–basic science and the resolution of the cancer problem: presidential address," *Cancer Research,* 53, 5890–5896, Dec., 1993.

K. Slowing et al., "Anti–inflammatory activity of leaf extracts of *Eugenia jambos* in rats," *J. of Ethnopharmacol.,* 43, 9–11, 1994.

L.A. Shamon et al., "A correlative approach for the identification of antimutagens that demonstrate chemopreventive activity," *Anticancer Res.,* 14, 1775–1778, 1994.

Y. Zhang et al., "Anticarcinogenic activities of sulforaphane and structurally related synthetic norbornyl isothiocyanates," *Proc. Natl. Acad. Sci., USA,* vol. 91, 3147–3150, Apr., 1994.

S. Sharma et al., "Screening of potential chemopreventive agents using biochemical markers of carcinogenesis," *Cancer Res.,* 54, 5848–5855, Nov. 1994.

N. Suh et al., "Discovery of natural product chemopreventive agents utilizing HL–60 cell differentiation as a model," *Anticancer Res.,* 15, 233–240, 1995.

C. Gerhauser et al., "Rotenoids mediate potent cancer chemopreventive activity through transcriptional regulation of ornithine decarboxylase," *Nature Med.,* vol. 1, No. 3, 260–266, Mar. 1995.

*Primary Examiner*—Jerome D. Goldberg
*Attorney, Agent, or Firm*—Marshall, O'Toole, Gerstein, Murray & Borun

[57] ABSTRACT

A composition and method of cancer chemoprevention is disclosed. The composition and method utilize resveratrol as a cancer chemopreventative agent in mammals, including humans.

16 Claims, 3 Drawing Sheets

□ resveratrol (3 mg/kg)
◇ resveratrol (8 mg/kg)
△ phenylbutazone (80 mg/kg)
▽ indomethacin (5 mg/kg)
○ control

CANCER CHEMOPREVENTATIVE COMPOSITION AND METHOD

This invention was made with government support under P01 CA48112 awarded by the National Cancer Institute.

FIELD OF THE INVENTION

The present invention relates to cancer chemopreventive compositions and methods. More particularly, the present invention relates to cancer chemoprevention in mammals, including humans, utilizing resveratrol as a cancer chemopreventive agent.

BACKGROUND OF THE INVENTION

Cancer claims over six million lives each year worldwide and is the largest single cause of death in both men and women. Extrinsic factors, including personal lifestyles, play a major role in the development of most human malignancies. Cigarette smoking, consumption of alcohol, exposure to synthetic and naturally occurring carcinogens, radiation, drugs, infectious agents, and reproductive and behavioral practices are widely recognized as important contributors to the etiology of cancer.

A surprising conclusion is that the human diet plays a causative role in more than one-third of human neoplasia. However, the human diet not only contains numerous mutagens and carcinogens, but also contains a variety of chemicals that block carcinogenesis in animal models. Chemoprevention, i.e., the prevention of cancer by ingestion of chemical agents that reduce the risk of carcinogenesis, therefore, is one of the most direct ways to reduce cancer-related morbidity and mortality. See, M. B. Sporn, *Fed. Proc.*, 38, 2528 (1979).

Dietary modifications can modulate cancer risk in various ways. For example, changes in caloric intake, altering the consumption of nutritive and nonnutritive diet components, and providing exposure to numerous minor chemicals that may be genotoxic or protective can increase or decrease the risk of cancer. Modifying the human diet to reduce the risk of cancer requires the identification of dietary carcinogens and chemopreventatives, even though interactions between the factors that modulate cancer risk are complex. Whereas extensive efforts have been made to identify dietary carcinogens and mutagens, the identification of chemopreventative agents has received less attention.

Cancer chemopreventive agents include nonsteroidal antiinflammatory drugs (NSAIDs), such as indomethacin, aspirin, piroxicam, and sulindac, all of which inhibit cyclooxygenase, abbreviated hereafter as COX. A COX inhibitory activity is important in cancer chemoprevention because COX catalyzes the conversion of arachidonic acid to proinflammatory substances, such as prostaglandins, which can stimulate tumor cell growth and suppress immune surveillance. O. J. Plescia et al., *Proc. Natl. Acad. Sci. U.S.A.*, 72, 1848 (1975), and J. S. Goodwin, *Am. J. Med.*, 77, 7 (1984). In addition, COX can activate carcinogens to forms that damage genetic material. T. V. Zenser et al., *J. Pharmacol. Exp. Ther.*, 227, 545 (1983), and D. Wild et al., *Carcinogenesis*, 8, 541 (1987).

There is a need in the art, therefore, for the identification of specific compounds that have a cancer chemopreventative effect on mammals. Such cancer chemopreventative compounds then can be used in drug compositions or as food additives to reduce the risk of cancer.

Investigators have searched for new cancer chemopreventative agents by evaluating hundreds of plant extracts for a potential to inhibit COX. An extract derived from *Cassia quinquangulata* Rich. (Leguminosae) was identified as a potent COX inhibitor, and on the basis of bioassay-guided fractionation, resveratrol (i.e., 3,5,4'-trihydroxy—transstilbene) was identified as the active compound. See, E. Mannila et al., *Phytochemistry*, 33, 813 (1993), and G. S. Jayatilake et al., *J. Nat. Prod.* 56, 1805 (1993).

SUMMARY OF THE INVENTION

The present invention is directed to cancer chemopreventative agents, compositions, and methods of using the chemopreventative agents to prevent carcinomas. In particular, the present invention is directed to compositions containing resveratrol, and use of the compositions in methods of cancer chemoprevention.

Resveratrol can be isolated from the roots of *C. quinquangulata* Rich. (Leguminosae), and other plant materials. The isolated resveratrol, or synthetic resveratrol, then can be used in compositions and methods of cancer chemoprevention.

An important aspect of the present invention, therefore, is to provide a method and composition for preventing tumor growth using resveratrol.

Another aspect of the present invention is to overcome the problem of high mammalian toxicity associated with synthetic cancer chemopreventative agents by using a natural product-derived compound, i.e., resveratrol.

Still another aspect of the present invention is to overcome the problem of insufficient availability associated with synthetic anticancer agents by utilizing readily available, and naturally occurring, resveratrol.

Yet another important aspect of the present invention is to provide a food product, or a food supplement, that contains resveratrol and can be used in methods of cancer chemoprevention.

Another important aspect of the present invention is to provide a drug composition containing resveratrol, and that can be administered to chemoprevent carcinomas.

These and other aspects of the present invention will become apparent from the following detailed description of the preferred embodiments of the invention.

DETAILED DESCRIPTION OF THE PREFERRED EMBODIMENTS

Figure 1:
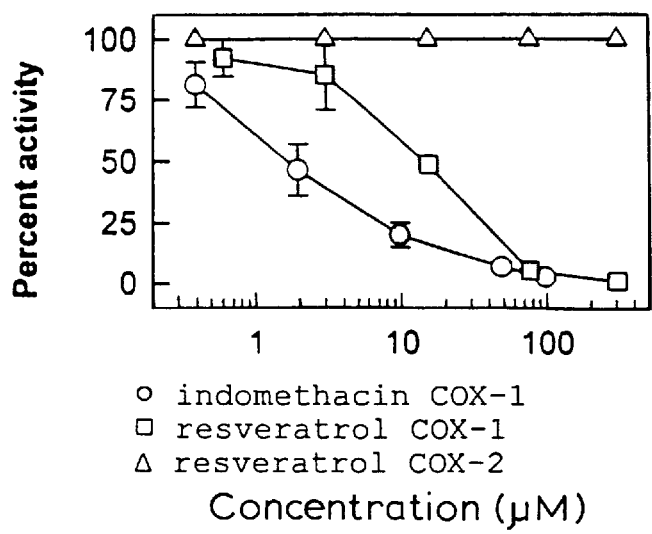
FIG. 1 contains plots of COX-1 and COX-2 activity vs. concentration of indomethacin and resveratrol.

Resveratrol, a phytoalexin found in grapes and other foods products, was purified and shown to have cancer chemopreventive activity in assays representing each of the three major stages of carcinogenesis, i.e., antiinitiation, antipromotion, and antiprogression. Resveratrol was found to act as an antioxidant and antimutagen, and to induce phase II drug-metabolizing enzymes (antiinitiation activity). Resveratrol also mediated antiinflammatory effects and inhibited cyclooxygenase and hydroperoxidase functions (antipromotion activity). In addition, resveratrol inhibited the development of preneoplastic lesions in carcinogen-treated mouse mammary glands in culture, and inhibited tumorigenesis in a mouse skin cancer model. As discussed in detail hereafter, these data show that resveratrol, a common constituent of the human diet, can be used in compositions and methods of cancer chemoprevention in mammals, including humans.

Resveratrol has the structural formula:

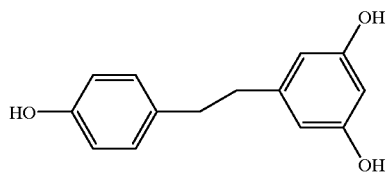

Resveratrol is relatively abundant in the plant kingdom, and is a common dietary constituent found in foods, such as grapes.

Resveratrol can be obtained, for example, from the dried roots of C. quinquangulata Rich., which are harvested in Peru. In particular, resveratrol was isolated as follows. Dried ground plant material (1 kg) was extracted twice overnight with methanol at room temperature, followed by concentration and dilution with water to give a water-methanol solution (1:9, v/v). After washing with hexane, the aqueous methanol layer was partitioned with ethyl acetate. The ethyl acetate extract (90 g) (88% inhibition of COX activity at 69 $\mu$g/ml) was separated into 28 fractions with chloroform-methanol (0 to 30% methanol) as eluent over a silica gel chromatographic column. Fractions 13 to 17 (66 to 85% inhibition of COX activity at 69 $\mu$g/ml) were combined (4 g), and the combined fractions were subjected to further column chromatography. The column was developed with chloroform-methanol (1 to 15% methanol) and hexaneethyl acetate (3:1 to 1:1) to afford an active compound (30 mg, 0.003%) that was assayed as having the formula $C_{14}H_{12}O_3$ by high-resolution mass spectral (MS) analysis. This compound was identified as resveratrol by comparison of physical data and $^1$H-nuclear magnetic resonance (NMR), $^{13}$C-NMR, and MS data to data from a known resveratrol sample.

Additional resveratrol for the studies disclosed herein was purchased from Sigma Chemical Co., St. Louis., Mo. The commercial resveratrol was evaluated by high-pressure liquid chromatography coupled with an MS analysis and found to be pure.

In general, the process of chemical carcinogenesis can be divided into three general stages, i.e., antiinitiation, antipromotion, and antiprogression activities. See, L. W. Wattenberg, Cancer Res. 53, 5890 (1993). Chemopreventive agents have been categorized according to which carcinogenesis stage they inhibit.

Resveratrol was found to inhibit cellular events associated with tumor initiation, promotion, and progression. As discussed hereafter, the activity of resveratrol was demonstrated on the basis of ability of resveratrol to inhibit the cyclooxygenase activity of COX-1 (i.e., median effective dose $ED_{50}$ of 15 $\mu$M). This activity correlates with antitumor promotion. Although the inhibitory activity of resveratrol was less than that of some NSAIDs, such as indomethacin ($ED_{50}$=2.3 $\mu$M), the resveratrol activity was much greater than the activity of compounds such as aspirin ($ED_{50}$=880 $\mu$M). Also, unlike indomethacin and most other NSAIDs, resveratrol inhibited the hydroperoxidase activity of COX-1 ($ED_{50}$=3.7 $\mu$M).

Resveratrol-mediated inhibition was specific for the cyclooxygenase activity of COX-1 because there was no discernable activity when oxygen uptake was assessed with COX-2, an inducible form of the enzyme associated with responses such as inflammation, and inhibition of the hydroperoxidase activity of COX-2 ($ED_{50}$=85 $\mu$M) was greatly reduced relative to the activity observed with COX-1.

Figure 2:
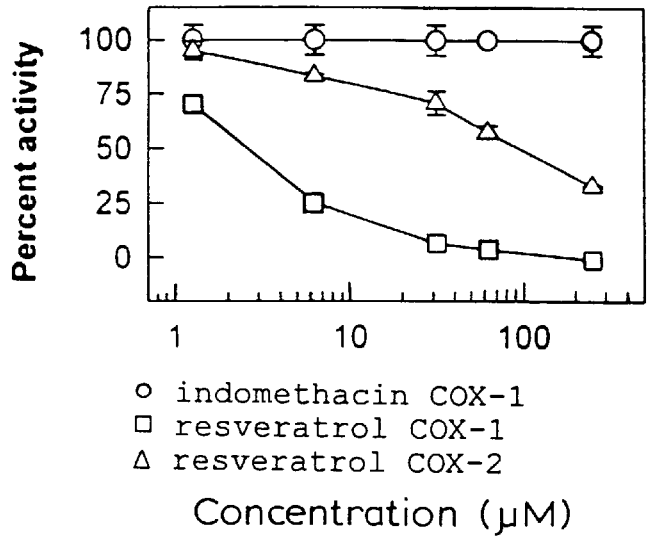
FIG. 2 contains plots of COX-1 and COX-2 hydroperoxidase activity vs. concentration of indomethacin and resveratrol.
Figure 3:
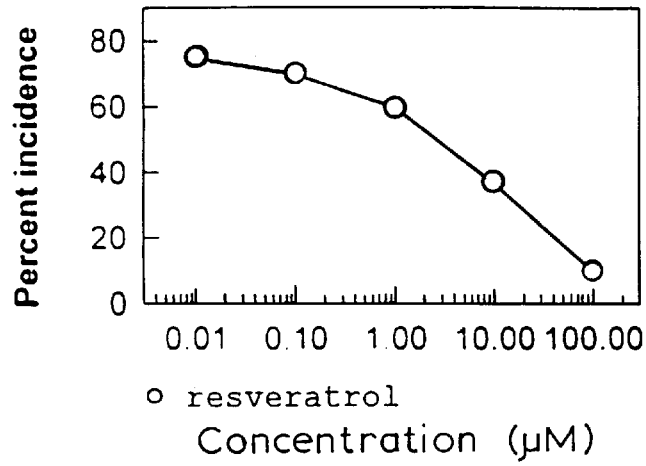
FIG. 3 is a plot of percent incidence of mouse mammary lesions vs. resveratrol concentration.

These results are illustrated in the plots of FIGS. 1–3. FIG. 1 shows the inhibitory effects of indomethacin on COX-1 and of resveratrol on COX-1 and COX-2. FIG. 1 contains plots of percent activity vs. concentration of indomethacin or resveratrol (in $\mu$M). COX activity was measured by measuring oxygen consumption at 37° C. The procedure is set forth in F. J. G. Van der Ouderaa et al., Methods Enzymol., 86, 60 (1982), and R. J. Kulmacz et al. in Prostaglandins and Related Substances. A Practical Approach, C. Benedetto et al., Eds. (IRL Press, Oxford, 1987), pp. 209–227, each incorporated herein by reference. The reactions were initiated by adding 0.6 mM arachidonic acid to a mixture containing 0.1 M (molar) sodium phosphate (pH 7.4), 1.0 mM (millimolar) phenol, and 0.01 mM hemin; microsomes (0.2 mg of protein) derived from sheep seminal vesicles were used as a crude source of COX-1 or recombinant human COX-2 (0.1 mg of protein); and the test compound. FIG. 1 shows the dramatic inhibitory effect of resveratrol on COX-1.

FIG. 2 shows the inhibitory effect of indomethacin on COX-1 hydroperoxidase activity, and resveratrol on COX-1 or COX-2 hydroperoxidase activity. Hydroperoxidase activity was determined by spectrophotometry. The reaction mixtures contained 0.1 M tris-NCl (pH 8.5), 1.2 $\mu$M (micromolar) hemin, 0.24 mM, N,N,N',N'-tetramethyl-p-phenylenediamine (TMPD), COX-1 (36 $\mu$g of protein) or COX-2 (45 $\mu$g of protein), and a test compound. Hydrogen peroxide (250 $\mu$M) was used to initiate the reaction, and changes in absorbence at 595 nm (nanometers) were measured. Inhibitory activity was calculated by comparing the initial rate of change in absorbance in the presence of a test compound with that observed with dimethyl sulfoxide (DMSO) solvent only. Each point represents the mean of two replicate determinations. FIG. 2 shows that resveratrol strongly inhibits COX-1 hydroperoxidase activity.

FIG. 3 shows the inhibition of DMBA-induced preneoplastic lesions in mouse mammary gland culture by treatment with resveratrol. Mammary glands were incubated with resveratrol for 10 days and DMBA, i.e., (7,12-dimethylbenz(a)anthracene), for 24 hours on day three. The procedure is set forth in R. C. Moon et al., in Chemistry and Biology of Retinoids, M. I. Dawson et al., Eds., CRC Press, Boca Raton, Fla., (1990), pp. 501–518, incorporated herein by reference. Percent incidence of mammary lesions was determined after an additional 14 days of incubation. The data from resveratrol-treated groups was compared to control groups and the results expressed as a percentage. Resveratrol demonstrated an excellent ability to inhibit DMBA-induced preneoplastic lesions in mouse mammary gland cultures.

Based on the results illustrated in FIGS. 1–3, the antiinflammatory activity of resveratrol was investigated. In a carrageenan-induced model of inflammation in rats, resveratrol significantly reduced pedal edema both in the acute phase (3 to 7 hours) and in the chronic phase (24 to 144 hours). The edema-suppressing activity of resveratrol was greater than that of phenylbutazone, and was similar to that of indomethacin. These data are set forth in FIG. 4. Overall, the data in FIG. 4 demonstrates the ability of resveratrol to inhibit tumor promotion.

Figure 4:
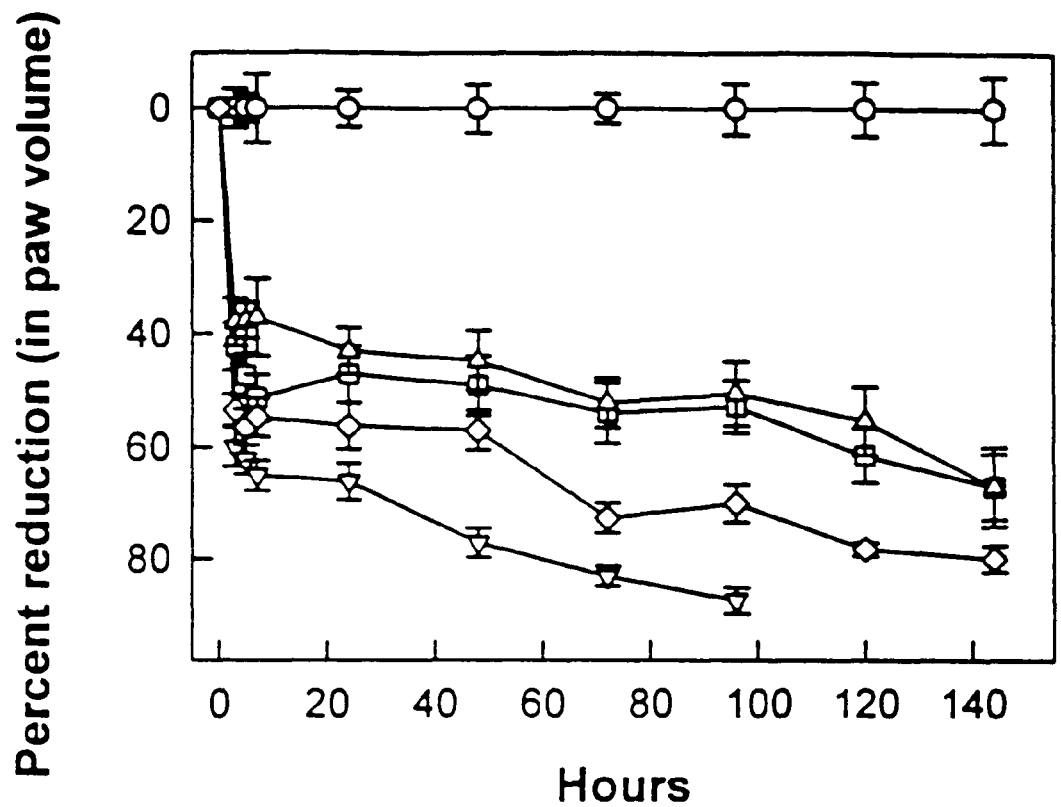
FIG. 4 contains plots of percent reduction in paw volume vs. time (hours) for carrageenan-induced inflammation in rats for various drugs vs. a control group.

In particular, FIG. 4 shows the effects of resveratrol (at 3 mg/kg and 8 mg/kg of body weight), phenylbutazone, and indomethacin on carrageenan-induced inflammation in rats. The procedure is set forth in K. Slowing et al., *J. Ethnopharmacol.*, 43, 9 (1994), incorporated herein by reference. In these tests, female Wistar rats (150 to 200 g body weight) were divided into groups of seven animals each. All rats received 0.1 ml of Freund's complete adjuvant, available from Sigma Chemical Co., St. Louis, Mo., by intradermal injection into the tail. Animals were used 7 days after injection of adjuvant. One hour after oral administration of resveratrol (3 or 8 mg per kilogram of body weight) or reference drugs including phenylbutazone (80 mg/kg) and indomethacin (5 mg/kg), the rats were injected with 0.1 ml of a 2% (w/v) suspension of carrageenan in saline solution into the left hind paw. For the control group, a 1:1 mixture of Tween 80 (i.e., polysorbate 80, available from ICI Americas, Inc., Wilmington, Del.) and water (0.2/3.3, v/v) and 1% (w/v) methylcellulose was used as a vehicle. The left hind paw volume of each rat was measured by water plethysmography on a Letica, Model L17500, before the adjuvant injection, and, again, 6 days later, before the injection of carrageenan. Paw volumes were determined within 3 to 144 hours after injection of carrageenan. Inhibition of edema was calculated relative to the mean edema of the vehicle-treated control group.

Percent reduction was determined by comparing the paw volume of rats in the control group (treated with carrageenan only) to paw volume of rats in the drug-treated group. Dosing was repeated daily for 7 days. Hours refers to hours after carrageenan injection. The data for the indomethacin group at 120 hours and 140 hours were not reliable because of the induction of secondary lesions. The plots in FIG. 4 show that resveratrol was effective in reducing carrageenan-induced inflammation in rats.

Resveratrol also was found to inhibit events associated with tumor initiation. For example, resveratrol inhibited free-radical formation ($ED_{50}$=27 μM), in a dose-dependent manner, when human promyelocytic leukemia (HL-60) cells were treated with 12-O-tetradecanoylphorbol-13-acetate (TPA). The procedure is set forth in S. Sharma et al., *Cancer Res.*, 54, 5848 (1994), incorporated herein by reference. In these tests, HL-60 cells were maintained in RPMI 1640 medium (available from Gibco BRL, Grand Island, N.Y.) supplemented with 5% heat-inactivated calf serum, penicillin G sodium (100 U/ml), and streptomycin sulphate (100 μg/ml) (Gibco BRL) at 37° C. in a humidified atmosphere at 5% carbon dioxide in air. Differentiation was induced by a 7-day treatment with 1.3% DMSO, and the cells were cultured in 96-well plates ($1 \times 10^6$ cells per well) in Hanks'balanced salt solution containing 30 mM Hepes, pH 7.6. After the addition of TPA (8 μM) to induce free radical formation, cytochrome c (160 μM) and resveratrol were added. The cells were incubated for 1 hour at 37° C., and antioxidant activity was determined by monitoring absorbance at 550 nm. The same reaction mixture, but lacking the HL-60 cells, was used as a blank control.

Resveratrol also functioned as an antimutagen, as illustrated by a dose-dependent inhibition of the mutagenic response induced by treatment of *Salmonella typhimurium* strain TM677 with 7,12-dimethylbenz (a) anthracene (DMBA) ($ED_{50}$=4μM) This procedure is set forth in L. A. Shamon et al., *Anticancer Res.*, 14, 1775 (1995), incorporated herein by reference. In these tests, a reaction mixture was prepared containing *Salmonella typhimurium* strain TM677, S9 liver homogenate derived from Aroclor 1254-pretreated rats, a NADPH-generating system (NADPH is the reduced form of nicotinamide adenine dinucleotide phosphate), and various concentrations of resveratrol, which were added one minute before the addition of 80 μM DMBA. After incubation for 2 hours at 37° C., the bacteria were recovered by centrifugation, resuspended, and plated (in triplicate) on minimal agar in the presence or absence of 8-azaguanine. The plates then were incubated for 48 hours at 37° C., and the results were expressed as mutant fractions, i.e., the average number of colonies capable of growing in the presence of 8-azaguanine divided by the average number of colonies capable of growing in the absence of 8-azaguanine, after correcting for dilution factors. The percent inhibition was calculated relative to control plates that were treated with DMSO only.

In addition, resveratrol induced quinone reductase activity with cultured mouse hepatoma (Hepa 1c1c7) cells (concentration required to double activity, 21 μM). See, H. J. Prochaska et al., *Anal. Biochem.*, 169, 328 (1988). This result is important because phase II enzymes, such as quinone reductase, are capable of metabolically detoxifying carcinogens. See, Y. Zhang et al., *Proc. Natl. Acad. Sci., U.S.A.*, 91, 3247 (1994). An identical response profile was observed with cultured BP'Cl hepatoma cells (a derivative of Hepa 1c 1c7 cells that is incapable of phase I enzyme induction), indicating that resveratrol is a monofunctional inducer.

In addition, the ability of resveratrol to inhibit the progression stage of carcinogenesis was tested by treating cultured HL-60 cells with resveratrol. See N. Suh et al., *Anticancer Res.*, 15, 233 (1995). Under normal culture conditions, these cells have unlimited proliferative capacity. In a dose-dependent manner, resveratrol-induced expression of nitroblue tetrazolium reduction activity, a marker of granulocyte formation ($ED_{50}$=11 μM), and nonspecific acid esterase activity, a marker of macrophase (monocyte) formation ($ED_{50}$=19 μM). Concurrently, incorporation of [$^3$H] thymidine was inhibited ($ED_{50}$=18 μM), which is indicative of terminal differentiation to a nonproliferative phenotype.

In order to more directly assess the cancer chemopreventive activity of resveratrol, the effects of resveratrol in a mouse mammary gland culture model of carcinogenesis was investigated. Resveratrol inhibited, in a dose-dependent manner, the development of DMBA-induced preneoplastic lesions ($ED_{50}$=3.1 μM) (see FIG. 3). No signs of toxicity were observed, as judged by morphological examination of the glands.

In addition, tumorigenesis in the two-stage mouse skin cancer model in which DMBA was used as initiator and TPA as promoter was studied. During an 18-week study, mice treated with DMBA-plus TPA developed an average of two tumors per mouse with 40% tumor incidence, as illustrated in FIG. 5(*a*).

Figure 5A:
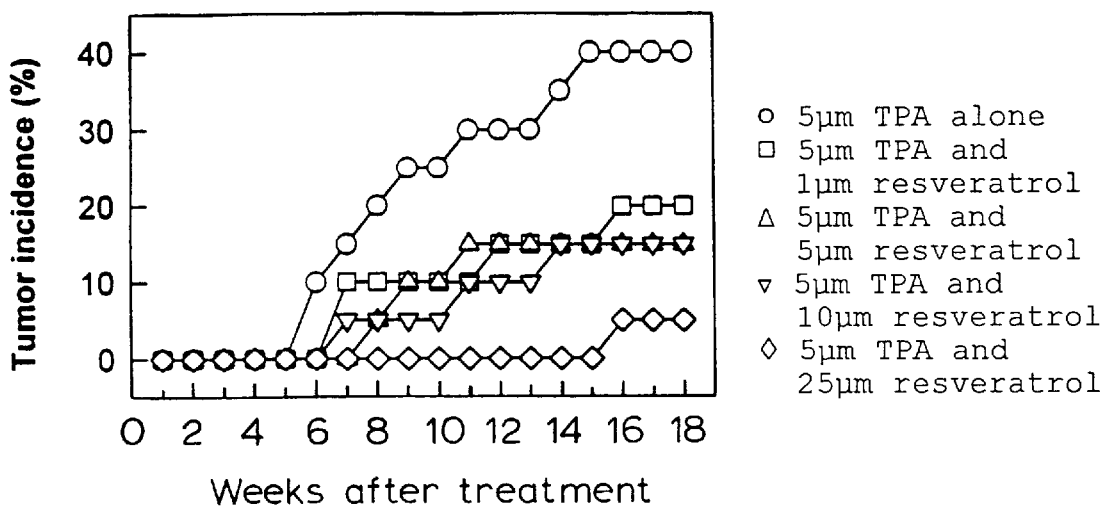
FIG. 5 contains plots of % tumor incidence ($a$) and number of tumors ($b$) vs. time after resveratrol treatment.
Figure 5B:
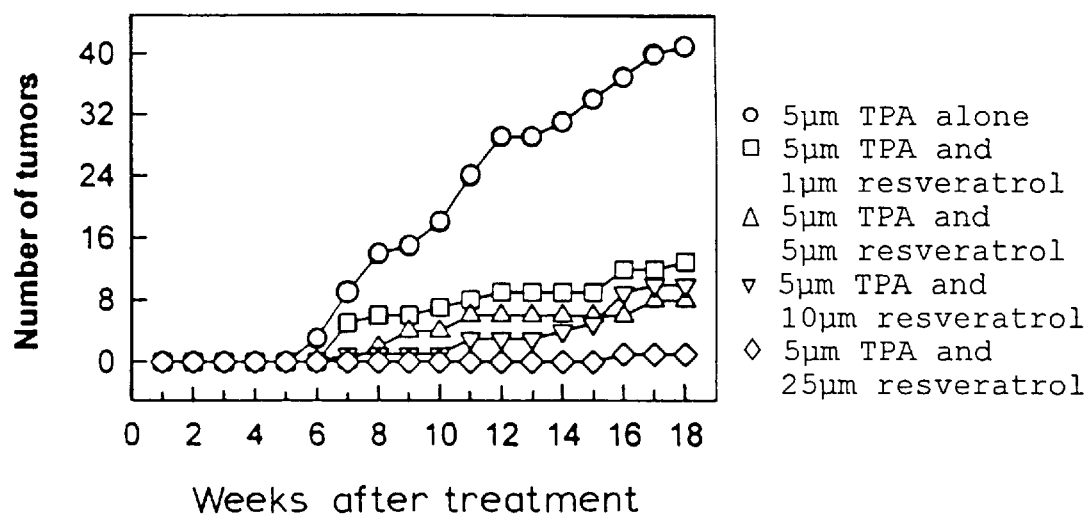

In particular, FIG. 5 shows the effect of resveratrol on tumorigenesis in the two-stage mouse skin model. Six groups of 20 female CD-1 mice (4 to 5 weeks old) were treated topically with 200 μmol of DMBA in 0.2 ml of acetone on the shaved dorsal region. See, C. Gerhäuser et al., *Nature Med.*, 1, 260 (1995). One week later, the mice were treated with 5 μmol of TPA in 0.2 ml of acetone alone or together with 1, 5, 10, or 25 μmol of resveratrol in 0.2 ml of acetone, twice a week for 18 weeks. Animals were weighed weekly and observed for tumor development once every week. FIG. 5A shows percent incidence of observable skin tumors. FIG. 5B shows total number of observable skin tumors. Overall, FIG. 5 shows that resveratrol greatly reduced the incidence of tumors in the mouse skin model.

Application of 1, 5, 10, or 25 μmol of resveratrol, together with TPA twice a week for 18 weeks, reduced the number of skin tumors per mouse by 68, 81, 76, and 98%, respectively, and the percentage of mice with tumors was lowered by 50, 63, 63, and 88%, respectively (FIG. 5(b)). No overt signs of resveratrol-induced toxicity were observed, as judged by visual inspection of the skin, gross morphological examination of major organ systems, or change in body weights, relative to controls.

To further demonstrate the ability of resveratrol to act as a cancer chemopreventive agent, tests were performed to determine whether resveratrol possesses activity against chemically induced neoplastic transformation in the C3H/10T1/2 clone 8 cells. This 10T1/2 cell line of mouse embryo fibro-blasts has been widely used as an experimental system to study neoplastic transformation induced by a variety of agents, such as polycyclic hydrocarbons, methylating agents, and X-rays. Two-stage transformation assays, with 3-methylcholanthrene (MCA) or DMBA as inducer and TPA as promoter, were performed in these tests.

C3H10T1/2 Cl 8 cells were purchased from the American Type Culture Collection (ATCC CCL 226, Rockville, Md.) and maintained in Eagle's basal medium with Earle's salts (EBME) containing 10% (v/v) fetal bovine serum (FBS, Gibco Laboratories, Chagrin Falls, Ohio) without antibiotics, and sodium bicarbonate (2.2 g/l). Cells were seeded at $5\times10^4$ per 75 cm$^2$ flask and grown in a humidified incubator containing 5% carbon dioxide in air at 37° C. Cells used in all these experiments were passage between 10–13.

Two-stage transformation assays in C3H10T1/2 cells were performed according to a procedure modified from that described in S. Mondal et al., Cancer Res., 36, 2254–2260 (1976).One thousand cells obtained from freshly confluent flasks were seeded per well in 12-well plate containing 2 ml of medium (12 wells per experimental point). After incubation at 37° C. for three days, MCA or DMBA (2 mg/ml stock solution in DMSO) was added to give final concentrations of 0.25 μg/ml. Carcinogen-containing medium was removed from the growing cultures after 24 hours and cells were rinsed once with PBS before addition of fresh EBME supplemented with 10% FBS and gentamycin (25 μg/ml). Following five days of further incubation without carcinogen, medium was changed to fresh medium containing TPA (0.1 μg/ml) or TPA and different concentrations of resveratrol. TPA and test compounds were added to the medium each time the medium was changed. Medium was changed on all plates twice weekly. After confluency was reached, the FBS concentration was reduced to 5% and amphotericin B (fungizone, 1.5 μg/ml) was added to the medium (see, C. A. Reznikoff et al., Cancer Res., 33, 3239–3249 (1973) and J. S. Bertram, Cancer Lett., 7, 289–298 (1979)). Subsequent medium changes were performed weekly. Cultures were fixed with methanol and stained with Giemsa at the seventh week. Type II and III transformed foci were scored according to the teachings of J. R. Landolph "Transformation Assay of Established Cell Lines: Mechanism and Application," pp. 185–199. Editors: T. Kakunaga et al., Oxford Univ. Press, Toronto (1985).

Table 1 summarizes the effects of various cancer chemopreventative agents, including resveratrol, on chemical-induced neoplastic transformation.

TABLE 1

Effects of various chemopreventive agents on chemical-induced neoplastic transformation

| Treatment | Total No. of type II | Total No. of type III | Total No. of foci/ no. wells scored | No. of wells foci/total no. of wells | Wells with foci (%) |
|---|---|---|---|---|---|
| 0.5% DMSO control | 0 | 0 | 0/12 | 0/12 | 0 |
| MCA (5.0)* | 9 | 2 | 11/12 | 8/12 | 67 |
| MCA (0.25) | 0 | 0 | 0/12 | 0/12 | 0 |
| MCA (0.25); TPA (0.1) | 8 | 0 | 8/12 | 7/12 | 58 |
| MCA (0.25); TPA (0.1); resveratrol 2.5 μM | 3 | 0 | 3/12 | 2/12 | 17 |
| MCA (0.25; TPA (0.1); resveratrol 5.0 μM | 3 | 1 | 4/12 | 2/12 | 17 |
| 0.5% DMSO control | 0 | 0 | 0/12 | 0/12 | 0 |
| MCA (0.25); TPA (0.1); resveratrol 10 | 1 | 0 | 1/12 | 1/12 | 8.3 |
| 0.5% DMSO control | 0 | 0 | 0/12 | 0/12 | 0 |
| DMBA (5.0) | 4 | 0 | 4/12 | 2/12 | 17 |
| DMBA (0.25) | 1 | 0 | 1/12 | 1/12 | 8.3 |
| DMBA (0.25); TPA (0.1) | 4 | 0 | 4/12 | 4/12 | 33 |
| DMBA (0.25); TPA (0.1); resveratrol 2.5 | 3 | 0 | 3/12 | 3/12 | 25 |
| DMBA (0.25); TPA (0.1); resveratrol 5.0 | 1 | 1 | 2/12 | 2/12 | 17 |
| 0.5% DMSO control | 0 | 0 | 0/12 | 0/12 | 0 |
| DMBA (0.25); TPA (0.1); resveratrol 10 μM | 1 | 1 | 2/12 | 2/12 | 17 |
| DMBA (0.25); TPA (0.1); aspirin 200 μM | 0 | 0 | 0/12 | 0/12 | 0 |
| DMBA (0.25); TPA (0.1); all-trans-retinyl acetate (0.3) | 0 | 0 | 0/12 | 0/12 | 0 |
| DMBA (0.25); TPA (0.1); Vit E. 100 μM | 4 | 0 | 4/12 | 4/12 | 33 |

*Numbers in parentheses, concentration (μg/ml).

The above tests and data show that resveratrol can be administered to mammals as a prophylactic against chemically induced cancers. Resveratrol can be formulated in suitable excipients for oral administration, for topical administration, or for parenteral administration. Such excipients are well known in the art. The resveratrol typically is present in such formulation in an amount of about 0.1% to about 75% by weight.

Pharmaceutical compositions containing resveratrol are suitable for administration to humans or other mammals. Typically, the pharmaceutical compositions are sterile, and contain no toxic, carcinogenic, or mutagenic compounds which would case an adverse reaction when administered.

Administration of resveratrol can be performed before, during, or after exposure to a carcinogen or procarcinogen. Suitable doses to be administered are sufficient to induce a measurable increase of phase II enzymes. The dosage of resveratrol typically will not exceed 500 μmol per kg per day, but can be much lower. Preferred dosages of resveratrol are about 0.005 to about 1 μmol per kg per day. To achieve the full advantage of the present invention, resveratrol is administered in a dosage of about 0.05 to about 0.75 μmol per kg per day.

Resveratrol is a known constituent of various plants. The physiological function of resveratrol in plants is not well defined. The compound is a phytoalexin, one of a group of compounds that are produced during times of environmental stress or pathogenic attack. Resveratrol has been found in at least 72 plant species, distributed in 31 genera and 12 families. A number of these plant species are components of the human diet, such as mulberries, peanuts, and grapes. Relatively high quantities of resveratrol are found in grapes, possibly because of the response of *Vitis vinifera* (Vitaceae) to fungal infection. Fresh grape skin contains about 50 to 100 μg of resveratrol per gram, and the concentration in red wine is in the range of 1.5 to 3 mg/liter. Appreciable amounts of resveratrol also are found in white and rose wines.

Resveratrol, therefore, can be isolated from various plant species, and used in drug formulations as a cancer chemopreventative agent. Alternatively, resveratrol to be added to food products as a cancer chemopreventative additive or supplement.

What is claimed is:

1. A method of chemopreventing cancer comprising administering a cancer chemopreventative composition to a mammal in need thereof in a sufficient amount to suppress the initiation, promotion, or progression of a cancer, said composition comprising resveratrol and said cancer selected from the group consisting of a mammary cancer, a skin cancer, human leukemia, a heptoma, a colon cancer, a chemically induced neoplastic transformation, and a neoplastic transformation due to oxidative damage.

2. The method of claim 1 wherein the composition is a solid.

3. The method of claim 1 wherein the composition is a liquid.

4. The method of claim 1 wherein the composition is administered topically.

5. The method of claim 1 wherein the composition is administered orally.

6. The method of claim 1 wherein the composition is administered parenterally.

7. The method of claim 1 wherein the composition is a food additive.

8. The method of claim 1 wherein the composition is a pharmaceutical.

9. The method of claim 1 wherein the composition is administered in a sufficient amount to provide a measurable increase in phase II enzymes.

10. The method of claim 1 wherein the composition is administered in an amount of about 0.005 to about 1 micromoles per kg per day.

11. The method of claim 1 wherein the composition is administered in an amount of about 0.05 to about 0.75 micromoles per kg per day.

12. The method of claim 1 wherein the composition is administered in an amount of about 0.075 to about 0.5 micromoles per kg per day.

13. The method of claim 1 wherein the composition is administered prior to exposure of the mammal to a carcinogen or a procarcinogen.

14. The method of claim 1 wherein the composition is administered during or after exposure of the mammal to a carcinogen or a procarcinogen.

15. The method of claim 1 wherein the mammal is a human.

16. The method of claim 15 wherein the composition is administered in a sufficient amount to produce a suppressing effect on a tumor associated with the cancer.

* * * * *